US008268362B2

(12) United States Patent
Braun et al.

(10) Patent No.: US 8,268,362 B2
(45) Date of Patent: Sep. 18, 2012

(54) MEDICINAL PRODUCT FOR THE PROMOTION OF WOUND HEALING

(75) Inventors: Friedrich Braun, Vienna (AT); Hans Peter Spängler, Vienna (AT); Johann Eibl, Vienna (AT)

(73) Assignee: Bio-Products & Bio-Engineering Aktiengesellschaft, Vienna (AT)

( * ) Notice: Subject to any disclaimer, the term of this patent is extended or adjusted under 35 U.S.C. 154(b) by 1539 days.

(21) Appl. No.: 10/819,848

(22) Filed: Apr. 7, 2004

(65) Prior Publication Data

US 2004/0191231 A1 Sep. 30, 2004

Related U.S. Application Data

(63) Continuation of application No. 09/351,985, filed on Jul. 12, 1999, now abandoned, which is a continuation of application No. PCT/AT98/00278, filed on Nov. 12, 1998.

(30) Foreign Application Priority Data

Nov. 12, 1997 (AT) ........................................ 1916/97

(51) Int. Cl.
 *A61K 35/18* (2006.01)
 *A61K 35/14* (2006.01)
 *A61K 38/18* (2006.01)
 *A61K 38/00* (2006.01)
(52) U.S. Cl. ......... 424/532; 424/533; 424/534; 514/7.6; 514/7.8; 514/8.2; 514/1.8
(58) Field of Classification Search .......... 424/532–534; 514/2
See application file for complete search history.

(56) References Cited

U.S. PATENT DOCUMENTS

| 4,160,025 | A | 7/1979 | Eibl et al. |
| 4,188,318 | A | 2/1980 | Shanbrom |
| 4,286,056 | A | 8/1981 | Andary et al. |
| 4,297,344 | A | 10/1981 | Schwinn et al. |
| 4,348,384 | A | 9/1982 | Horikoshi et al. |
| 4,395,396 | A | 7/1983 | Eibl et al. |
| 4,427,650 | A | 1/1984 | Stroetmann |
| 4,427,651 | A | 1/1984 | Stroetmann |
| 4,440,679 | A | 4/1984 | Fernandes et al. |
| 4,442,655 | A | 4/1984 | Stroetmann |
| 4,710,381 | A | 12/1987 | Kunicki et al. |
| 4,814,435 | A | 3/1989 | Schwarz et al. |
| 4,923,815 | A | 5/1990 | Tanaka et al. |
| 5,004,604 | A | 4/1991 | Terness et al. |
| 5,149,787 | A | 9/1992 | Kunicki et al. |
| 5,165,938 | A | 11/1992 | Knighton |
| 5,175,087 | A | 12/1992 | Ranby et al. |
| 5,178,883 | A | 1/1993 | Knighton |
| 5,185,160 | A | 2/1993 | Chao |
| 5,254,536 | A | 10/1993 | Racanelli et al. |
| 5,278,289 | A | 1/1994 | Johnson et al. |
| 5,457,181 | A | 10/1995 | Michalski et al. |
| 5,484,890 | A | 1/1996 | Johnson et al. |
| 5,514,579 | A | 5/1996 | O'Hara et al. |
| 5,552,290 | A | 9/1996 | Michelson et al. |
| 5,589,462 | A | 12/1996 | Patat et al. ........................ 514/21 |
| 5,614,500 | A | 3/1997 | Zimmermann |
| 5,618,663 | A | 4/1997 | Delmas ............................ 435/2 |
| 5,631,011 | A | 5/1997 | Wadstrom |
| 5,645,540 | A | 7/1997 | Henniges et al. |
| 5,697,980 | A | 12/1997 | Otani et al. |
| 5,739,288 | A | 4/1998 | Edwardson |
| 5,804,400 | A | 9/1998 | Martin et al. |
| 5,874,407 | A | 2/1999 | Kelley et al. |
| 5,902,608 | A | 5/1999 | Read et al. ..................... 424/532 |
| 5,980,888 | A | 11/1999 | Dimoudis .................... 424/93.7 |
| 5,981,254 | A | 11/1999 | Bui-Khac |
| 6,054,122 | A | 4/2000 | MacPhee et al. |
| 6,358,534 | B1 | 3/2002 | Schwarz et al. |
| 7,371,722 | B2 | 5/2008 | Eibl |
| 7,494,971 | B2 | 2/2009 | Eibl |
| 2001/0033837 | A1 | 10/2001 | Metzner et al. |
| 2002/0001624 | A1 | 1/2002 | Braun |
| 2002/0034809 | A1 | 3/2002 | Teschner et al. |
| 2002/0114796 | A1 | 8/2002 | Eibl |
| 2004/0082511 | A1 | 4/2004 | Watzek |
| 2005/0192223 | A1 | 9/2005 | Eibl |
| 2006/0009376 | A1 | 1/2006 | Eibl |
| 2009/0123453 | A1 | 5/2009 | Eibl |
| 2009/0275011 | A1 | 11/2009 | Eibl |

FOREIGN PATENT DOCUMENTS

| CA | 2156991 | 2/1996 |
| CA | 2302224 | 3/1999 |
| DE | 19824306 | 11/1999 |
| EP | 0270291 | 6/1988 |
| EP | 0534178 | 3/1993 |
| EP | 0680764 | 11/1995 |
| EP | 0700684 | 5/1996 |
| EP | 1161958 | 12/2001 |
| GB | 2102811 | 2/1983 |
| JP | 9286797 | 11/1997 |

(Continued)

OTHER PUBLICATIONS

Valeri et al., 1974, "A Simple Method for Freezing Human Platelets Using 6% Dimethylsulfoxide and Storage at −80°C", Blood 43(1):131-136.
SU353724 WPI/Derwent Abstract, AN 73-31168U/197322, 1973.
U.S. Appl. No. 09/351,985, Aug. 15, 2000 Non-Final Rejection.
U.S. Appl. No. 09/351,985, Feb. 21, 2001 Response after Non-Final Action.
U.S. Appl. No. 09/351,985, May 3, 2001 Non-Final Rejection.
U.S. Appl. No. 09/351,985, Aug. 3, 2001 Response after Non-Final Action.
U.S. Appl. No. 09/351,985, Oct. 30, 2001 Non-Final Rejection.
U.S. Appl. No. 09/351,985, Jan. 31, 2002 Response after Non-Final Action.

(Continued)

Primary Examiner — Shengjun Wang
(74) Attorney, Agent, or Firm — Baker Botts L.L.P.

(57) ABSTRACT

The invention relates to a medicinal product for topical use for the promotion of wound healing, which comprises thrombocytes or thrombocyte fragments, wherein the thrombocytes or thrombocyte fragments contain growth factors and are capable of releasing the same and are present in the lyophilized or deep-frozen state and have been subjected to a process for virus partitioning and/or virus inactivation.

19 Claims, No Drawings

FOREIGN PATENT DOCUMENTS

| WO | 9734614 | 9/1957 |
|---|---|---|
| WO | WO8102105 | 8/1981 |
| WO | WO8603122 | 6/1986 |
| WO | WO9007931 | 7/1990 |
| WO | WO9012581 | 11/1990 |
| WO | WO9104035 | 4/1991 |
| WO | WO9113905 | 9/1991 |
| WO | WO9116009 | 10/1991 |
| WO | 9117655 | 11/1991 |
| WO | WO9305067 | 3/1993 |
| WO | 9323997 | 12/1993 |
| WO | WO9911301 | 3/1999 |
| WO | WO9924044 | 5/1999 |
| WO | WO0015248 | 3/2000 |
| WO | WO0071153 | 11/2000 |

OTHER PUBLICATIONS

U.S. Appl. No. 09/351,985, Apr. 16, 2002 Final Rejection.
U.S. Appl. No. 09/351,985, Oct. 18, 2002 Notice of Appeal Filed.
U.S. Appl. No. 09/351,985, Dec. 23, 2002 Request for Continued Examination (RCE); Response to Final Rejection.
U.S. Appl. No. 09/351,985, Mar. 26, 2003 Non-Final Rejection.
U.S. Appl. No. 09/351,985, Jul. 25, 2003 Response after Non-Final Action.
U.S. Appl. No. 09/351,985, Oct. 7, 2003 Final Rejection.
U.S. Appl. No. 09/351,985, Jul. 28, 2004 Abandonment.
U.S. Appl. No. 09/998,575, Sep. 29, 2003 Requirement for Restriction/Election.
U.S. Appl. No. 09/998,575, Dec. 3, 2003 Response to Election/Restriction Filed.
U.S. Appl. No. 09/998,575, Jan. 2, 2004 Response to Election/Restriction Filed.
U.S. Appl. No. 09/998,575, Mar. 12, 2004 Non-Final Rejection.
U.S. Appl. No. 09/998,575, Jul. 12, 2004 Informal or Non-Responsive Amendment; Petition.
U.S. Appl. No. 09/998,575, Nov. 29, 2004 Petition Decision.
U.S. Appl. No. 09/998,575, Jan. 21, 2005 Response after Non-Final Action.
U.S. Appl. No. 09/998575, May 4, 2005 Non-Final Rejection.
U.S. Appl. No. 09/998,575, Oct. 7, 2005 Response after Non-Final Action.
U.S. Appl. No. 09/998,575, Dec. 27, 2005 Final Rejection.
U.S. Appl. No. 09/998,575, Jul. 21, 2006 Abandonment.
U.S. Appl. No. 10/621,894, Jan. 31, 2005 Requirement for Restriction/Election.
U.S. Appl. No. 10/621,894, May 2, 2005 Response to Election/Restriction Filed.
U.S. Appl. No. 10/621,894, Jul. 25, 2005 Response to Election/Restriction Filed.
U.S. Appl. No. 10/621,894, Sep. 7, 2005 Non-Final Rejection.
U.S. Appl. No. 10/621,894, Mar. 10, 2006 Response after Non-Final Action.
U.S. Appl. No. 10/621,894, Jun. 2, 2006 Final Rejection.
U.S. Appl. No. 10/621,894, Dec. 27, 2006 Response after Final Action/RCE.
U.S. Appl. No. 10/621,894, Mar. 1, 2007 Non-Final Rejection.
U.S. Appl. No. 10/621,894, Jul. 19, 2007 Response after Non-Final Action.
U.S. Appl. No. 10/621,894, Sep. 14, 2007 Final Rejection.
U.S. Appl. No. 10/621,894, Oct. 31, 2007 Response after Final Action/RCE.
U.S. Appl. No. 10/621,894, Feb. 12, 2008 Non-Final Rejection.
U.S. Appl. No. 10/621,894, Aug. 11, 2008 Response after Non-Final Action.
U.S. Appl. No. 10/621,894, Dec. 2, 2008 Final Rejection.
U.S. Appl. No. 10/621,894, Jun. 2, 2009 Response after Final Action/RCE.
U.S. Appl. No. 10/621,894, Aug. 14, 2009 Non-Final Rejection.
U.S. Appl. No. 10/621,894, Feb. 16, 2010 Response to Non-Final Rejection.
U.S. Appl. No. 11/155,416, Feb. 22, 2006 Non-Final Rejection.
U.S. Appl. No. 11/155,416, Jun. 22, 2006 Response after Non-Final Action.
U.S. Appl. No. 11/155,416, Aug. 9, 2006 Final Rejection.
U.S. Appl. No. 11/155,416, Jan. 9, 2007 Response after Final Action/RCE.
U.S. Appl. No. 11/155,416, May 5, 2007 Non-Final Rejection.
U.S. Appl. No. 11/155,416, Jul. 12, 2007 Response after Non-Final Action.
U.S. Appl. No. 11/155,416, Oct. 3, 2007 Requirement for Restriction/Election.
U.S. Appl. No. 11/155,416, Jan. 24, 2008 Response to Election/Restriction Filed.
U.S. Appl. No. 11/155,416, Apr. 7, 2008 Non-Final Rejection.
U.S. Appl. No. 11/155,416, Oct. 6, 2008 Response after Non-Final Action.
U.S. Appl. No. 11/155,416, Jan. 23, 2009 Final Rejection.
U.S. Appl. No. 11/155,416, Jul. 1, 2009 Response after Final Action/RCE.
U.S. Appl. No. 11/155,416, Sep. 21, 2009 Non-Final Rejection.
U.S. Appl. No. 11/155,416, Mar. 22, 2010 Response to Non-Final Rejection.
U.S. Appl. No. 11/041,165, May 16, 2006 Requirement for Restriction/Election.
U.S. Appl. No. 11/041,165, Jul. 19, 2006 Response to Election/Restriction Filed.
U.S. Appl. No. 11/041,165, Aug. 14, 2006 Non-Final Rejection.
U.S. Appl. No. 11/041,165, Feb. 14, 2007 Response after Non-Final Action.
U.S. Appl. No. 11/041,165, Jun. 25, 2007 Non-Final Rejection.
U.S. Appl. No. 11/041,165, Dec. 18, 2007 Response after Non-Final Action.
U.S. Appl. No. 11/041,165, Mar. 17, 2008 Final Rejection.
U.S. Appl. No. 11/041,165, Jul. 17, 2008 Response after Final Action/Terminal Disclaimer Filed.
U.S. Appl. No. 11/041,165, Sep. 16, 2008 Notice of Appeal Filed.
U.S. Appl. No. 11/041,165, Oct. 21, 2008 Amendment After Final.
U.S. Appl. No. 11/041,165, Oct. 21, 2008 Notice of Allowance and Fees Due.
U.S. Appl. No. 11/040,891, Sep. 7, 2006 Requirement for Restriction/Election.
U.S. Appl. No. 11/040,891, Dec. 11, 2006 Response to Election/Restriction Filed.
U.S. Appl. No. 11/040,891, Apr. 6, 2007 Response to Election/Restriction Filed.
U.S. Appl. No. 11/040,891, Jul. 5, 2007 Non-Final Rejection.
U.S. Appl. No. 11/040,891, Jan. 2, 2008 Response after Non-Final Action.
U.S. Appl. No. 11/040,891, Jan. 3, 2008 Terminal Disclaimer Filed.
U.S. Appl. No. 11/040,891, Jan. 24, 2008 Notice of Allowance and Fees Due.
U.S. Appl. No. 12/355,507, Feb. 3, 2010 Non-Final Rejection.
Exner et al. Blood Coagulation and Fibrinolysis. 2003, 14:773-779.
Boulanger, C. M. et al. "Circulating microparticles: a potential prognostic marker for atherosclerotic vascular disease." Hypertension. (2006) 48: 180-186.
Reininger, A. J. et al. "Mechanism of platelet adhesion to von Willebrand factor and microparticle formation under high shear stress." Blood. (2006) 107:3537-3545.
Simak, J., Gelderrnan, M.P. "Cell membrane microparticles in blood and blood products: potentially pathogenic agents and diagnostic markers." Transfus Med Rev. (2006)20: 1-26.
Freyssinet, J. M. "Cellular microparticles: what are they bad or good for?" J Thromb Haemost. (2003) I: 1655-1662.
VanWijk, M. J. et al. "Microparticles in cardiovascular diseases." Cardiovasc Res. (2003)59:277-287.
Zwaal, R. F., Schroit, A. J. "Pathophysiologic implications of membrane phospholipid asymmetry in blood cells." Blood. (1997)89: 1121-1132.
Connor, J. et al. "Bidirectional transbilayer movement of phospholipid analogs in human red blood cells. Evidence for an ATP-dependent and protein-mediated process." J BioI Chem. (1992)267: 19412-19417.
Wiedmer, T., Sims, P. 1. "Participation of protein kinases in complement C5b-9-induced shedding of platelet plasma membrane vesicles." Blood. (1991 )78:2880-2886.

George, J. N. et al. "Platelet membrane glycoprotein changes during the preparation and storage of platelet concentrates." Transfusion. (1988)28: 123-126.
Seigneuret, M., Devaux PF. "ATP-dependent asymmetric distribution of spin-labeled phospholipids in the erythrocyte membrane: relation to shape changes." Proc Natl Acad Sci USA. (1984)81:3751-3755.
George, J. N. et al. "Isolation of human platelet membrane microparticles from plasma and serum." Blood. (1982)60:834-840.
Wolf, P. "The nature and significance of platelet products in human plasma." Br J Haematol. (1967)13:269-288.
Zeng . The Southeast Asian Journal of Tropical Medicine and Public Health. 1993. vol. 24, Suppl. 1, pp. 204-205.
Horstman LL, Ahn YS. Platelet microparticles: a wide-angle perspective Crit Rev Oncol Hematol. Apr. 1999;30(2): 111-42.
Heraud, F. Ann Rheum Dis 2000, "Apoptosis in normal and osteoarthritic human articular cartilage", pp. 959-965.
Weber et al., Thromb Res, 2000, "Platelet-Derived Microparticles Stimulate Coronary Artery Smooth Muscle Cell Mitogenesis by a PDGF-Independent Mechanism", pp. 461-466.
Forlow et al., Blood 2000, "Leukocyte-leukocyte interactions mediated by platelet microparticles under flow", pp. 1317-1323.
Barnes et al., JBMR, 1999, "Perspective Growth Factor Regulation of Fracture Repair", pp. 1805-1815.
Gornstein et al., 1. Periodontal, 1999, "Androgens modulate interleukin-6 production by gingiral fibroblasts in vitra", pp. 604-609.
Barry et al., 1. Clin. Invest., Thromb Haemat, 1999, "Transcellular Activation of Platelets and Endothelial Cells by Bioactive Lipids in Platelet Microparticles", pp. 2118-2127.
Barry et al., J. Clin. Invest., 1997, "Mechanisms of Cellular Activation by Platelet Microparticles", pp. 794-800.
Holzheimer et al., RG, 1996, Zentralbi Chir, "Lokale und systemische immunologische Aspekte in Klinik und Experiment", pp. 31-32.
Gawaz et al., M. Aterioscler Thromb. Vase. Biol., 1996, "Agglutination of Isolated Platelet Membranes".
Brittberg et al., The New England Journal of Medicine, 1994, "Treatment of Deep Cartilage Defects in the Knee with Autologous Chondrocyte Transplantation".
Bennet et al., Am J. Surg., 1993, "Growth Factors and Wound Healing: Part II. Role in Normal and Chronic Wound Healing", pp. 74-81.
Bennet et al., Am J. Surg., 1993, "Growth Factors and Wound Healing: Biochemical Properties of Growth Factors and Their Receptors", pp. 728-737.
Piquet et al., Vox Sang, 1992, "Virus Inactivation of Fresh Frozen Plasma by a Solvent DeterQent Procedure: Biological Results" oos. 251-256.
Hoffman et al., M. Thromb Haemat, 1992, "Coagulation Factor IXa Binding to Activated Platelets and Platelet-Derived Microparticles: A Flow Cytometric Study", pp. 74-78.
Horowitz et al., Blood 1992, "SolventiDetergent-Treated Plasma: A Virus-Inactivated Substitute for Fresh Frozen Plasma", pp. 826-831.
Tans et al., Blood 1991, "Comparison of Anticoagulant and Procoagulant Activities of Stimulated Platelets and Platelet-Derived Microparticles", pp. 2641-2648.
Piet et al., Transfusion 1990, "The use of tri(n-butyl)phosphate detergent mixtures to inactivate hepatitis viruses and human immunodeficiency virus in plasma and plasma's subsequent fractionation" pp. 591-598.
Lin et al., Blood 1989, "Use of 8-Methoxypsoralen and Long-Wavelength Ultraviolet Radiation for Decontamination of Platelet Concentrates", pp. 517-525.
Ando et al., J. Biol. Chern. 1988, "Complement Proteins C5b-9 Cause Release of Membrane Vesicles from the Platelet Surface That Are Enriched in the Membrane Receptor for Coagulation Factor Va and express Prothrombinase Activity", pp. 18205-18212.
Sims et al., J. Biol. Chern. 1988, "Complement Proteins C5b-9 Initiate Secretion of Platelet Storage Granules without Increased Binding of Fibrinogen or von Willerbrand Factor to Newly Expressed Cell Surface GPIIb-IIIa", pp. 11907-11914.
George et al., J. Clin. Invest., 1986, "Studies on Resting and Activated Platelets and Platelet Membrane Microparticles in Normal Subjects, and Observations in Patients during Adult Respiratory Distress Syndrome and Cardiac Surgery", pp. 340-348.
George et al., Blood 1986, "Platelet membrane microparticles in blood bank fresh frozen plasma and cryoprecipitate", pp. 307-309.
Goodson et al., J. Surg. Res., 1977, "Studies of Wound Healing in Experimental Diabetes Mellitus", pp. 221-227.
Search Report for PCT/AT2002/00018.
Lammle and Griffin, 1985, "Formation of the fibrin clot: the balance of procoagulant and inhibitory factors," Clinics in Haematology 14(2):281-342.
European Pharmacopoeia Suppl. 4.5. Jul. 2003, p. 3687.
European Pharmacopoeia (Eur.Pharm.4.sup.th Edition 2002, pp. 123-126, 2.6.1. Sterility. pp. 131-132, 2.6.8. Pyrogens.
Blomback B. Fibrinogen: Evolution of the Structure-Function Concept: Keynote Address at Fibrinogen 2000 Congress. Annals N.Y. Acad.Sci. 2001; 936:1-10.
Booth N.A. TAFI Meets the Sticky Ends. Thromb.Haemost. 2001; 85:1-2.
Siebenlist K.R., Meh D.A., Mosesson M.W. Protransglutaminase (F-XIII) mediated cross-linking of fibrinogen and fibrin. Thromb. Haemost.2001; 86:1221-1228.
Rapaport S.I., Rao, L.V.M. The Tissue Factor Pathyway: How it has become a "Prima Ballerina". Thromb.Haemost.1995; 74-7-17.
Von dem Borne P.A.K., Koppelman S.J., Bouma B.N. et al. Surface independent factor XI activation by thrombin in the presence of high molecular weight kininogen. Thromb.Haemost.1994; 72:397-402.
Drake T.A., Morrissey J.H., Edgington T.S. Selective cellular expression of tissue factor in human tissue. Implication for disorders of hemostasis and thrombosis. Am.J.Path.1989; 134:1087-1097.
Mann K.G., Jenny R.J., Krishnaswamy. Cofactor proteins in the assembly and expression of blood clotting enzyme complexes. Ann. Rev.Biochem.1988; 57:915-956.
Matras H. et. Al. Zur Klebung von Nervenanstomosen mit Gerinnungssubstanzen. Fortschr.Kiefer-Gesichts-Chir.1976; 112-114.
Spangler H.P. Gewebeklebung und lokale Blutstillung mit Fibrinogen, Thrombin und Blutgerinnungsfaktor XIII (Experimentelle Untersuchungen und klinische Erfahrungen). Wien.klin.Wschr. 1976; 88(4):3-18.
Davie E.W., Ratnoff O.D. Waterfall sequence for intrinsic blood clotting. Science 1964; 145-1310-1312.
MacFarlane R.G. An enzyme cascade in the blood clotting mechanism and its function as a biochemical amplifier. Nature 1964; 202:498-499.
Young F. et al. "Suture" of Wounds by Plasma-Thrombin Adhesion. War Med.1944; 6:80-85.
Grey E.G. Fibrin as a haemostatic in cerebral surgery. Surg. Gyn. Obst.1915; 21-452-445.
Morawitz P. Die Chemie der Blutgerinnung. Ergebn.d.Physiol.1905; 4:307.
Butenas et al., "Normal" Thrombin Generation, Blood, 1999, 94:2169-2178.
Search Report for PCT/AT2003/000208 (translation).
Search Report for PCT/AT2003/000204 (translation).
[Retreived from] http://www.thefreedictionary.com/allogenic, 2009, 3 pages [Retrieved on Sep. 9, 2009].
[Retrieved from] 'http://en.wikipedia.org/wikilProtease', 3 pages, Jan. 26, 2007 [retrieved on Jan. 26, 2007].
Tolo, et al., Journal of Interferon and Cytokine Research, 21, 913-920.
Hemker HC. Thrombin Generation in a Reconstituted System: A Comment. Thromb Haemost 2002; 87:551-552.
Mann et al., Thrombin Generation in a Reconstituted System: A Reply. Thromb Haemost 2002; 87:552-554.
Mutch et al., Human Thrombi Contain an Abundance of Active Thrombin. Thromb Haemost 2001; 86:1028-1034.
Siebenlist et al., Protansglutaminase (Factor XIII) Mediated Crosslinking of Fibrinogen and Fibrin. Thromb Haemost 2001; 86:1221-1228.
Brummel et al., An Integrated Study of Fibrinogen during Blood Coagulation. J Biol Chem 1999; 274:22862-22870.

Fischer et al., Immobilized hirudin and hirudin-based peptides used for the purification of recombinant human thrombin prepared from recombinant human prothrombin. Protein Expr Purif. 1996 8(2):167-174.

Feldman et al., Large-scale preparation and biochemical characterization of a new high purity factor IX concentrate prepared by metal chelate affinity chromatography. Blood Coagul Fibrinolysis. 1994, 5(6):939-948.

Lawson et al.,. A Model for the Tissue Factor Pathway to Thrombin. J Biol Chem 1994; 269:23357-23366.

Kulseth et al., A highly sensitive chromogenic microplate assay for quantification of rat and human plasminogen. Anal Biochem. 1993, 210,(2): 314-317.

Andersson et al., Isolation and characterization of human factor VIII: Molecular forms in commercial factor VIII concentrate, cryoprecipitate, and plasma. Proc Natl Acad Sci 1986; 83:2979-2983.

Eaton et al. Proteolytic Processing of Human Factor VIII. Correlation of Specific Cleavages by Thrombin, Factor Xa, and Activated Protein C with Activation and Inactivation of Factor VIII Coagulant Activity. Biochemistry 1986; 25:505-512.

Rotblat et al., Purification of Human Factor VIII:C and Its Characterization by Western Blotting Using Monoclonal Antibodies. Biochemistry 1985; 24:4294-4300.

Monsigny et al., Assay for proteolytic activity using a new fluorogenic substrate (peptidyl-3-amino-9-ethyl-carbazole); quantitative determination of lipopolysaccharide at the level of one picogram. EMBO J. 1982;1(3):303-306.

Search Report for PCT/AT2003/00374.

Fredenburgh et al. Conformational changes in thrombin when complexed by serpins. J Biol Chem. Nov. 30, 2001;276(48):44828-34.

Preissner et al. Vitronectin: a new molecular connection in haemostasis.Thromb Haemost. Aug. 1, 1991;66(2):189-94.

Kruithof et al. Plasminogen Activator Inhibitor 1:Development of a Radioimmunassay and Observations on its Plasma Concentration During Venoius Occlusion and After Platelet Aggregation. Blood. Nov. 1987 70:1645-1653.

Castellino et al. Enhancement of the streptokinase-induced activation of human plasminogen by human fibrinogen and human fibrinogen fragment D1 . Ann N Y Acad Sci. Jun. 27, 1983;408:595-601.

Clark et al. Fibronectin and fibrin provide a provisional matrix for epidermal cell migration during wound reepithelialization. J Invest Dermatol. Nov. 1982;79(5):264-9.

Sakata et al. Cross-linking of alpha 2-plasmin inhibitor to fibrin by fibrin-stabilizing factor.J Clin Invest. Feb. 1980;65(2):290-7.

Matras et al. Suture-free interfascicular nerve transplantation in animal experiments Wien. Med Wochenschr. Sep. 9, 1972; 122(37):517-23.

Thorsen et al. Differences in the binding to fibrin of urokinase and tissue plasminogen activator.Thromb Diath Haemorrh. Aug. 31, 1972;28(1):65-74.

Mosesson et al. The cold-insoluble globulin of human plasma. I. Purification, primary characterization, and relationship to fibrinogen and other cold-insoluble fraction components.J Biol Chem. Nov. 10, 1970;245(21):5728-36.

Irving et al., "Phylogeny of the Serpin Superfamily: Implications of Patterns of Amino Acid Conservation for Structure and Function." Dec. 2000, Genome Research, 10(12):1845-1864.

Bird, PI, "Serpins and regulation of Cell Death." 1998, Results Probl. Cell Differ., 24:63-89.

Carrell et al., 1986, "Serpins: a Family of Serine Protease Inhibitors" in "Protease Inhibitors," New York, Elsevier, pp. 403-420.

Worrall et al., "The Expanding Superfamily of Serpins: Searching for the Real Targets." 1999, Biochem. Soc. Trans., 27(4), 746-50.

Burnouf, T., "Examples of virus inactivation treatment in plasma derivatives manufacturing," Colloque INSERM (1989), 175 (Biotechnol. Proteins Plasma): 373-81.

Search Report for PCT/AT00/00141.

Brass et al., 1978, "Fibrin Formation: Effect of Calcium Ions," Blood 52(4):654-658.

MEDICINAL PRODUCT FOR THE PROMOTION OF WOUND HEALING

CROSS REFERENCE TO RELATED APPLICATION(S)

The present application is a continuation of U.S. patent application Ser. No. 09/351,985, filed Jul. 12, 1999 now abandoned, which is a continuation of International Patent Application No. PCT/AT98/00278, filed Nov. 12, 1998, published in German on May 20, 1999 as International Patent Publication No. WO99/24044, which claims priority to Austrian Application No. A 1916/97, filed Nov. 12, 1997, all of which are incorporated herein in their entireties.

This invention relates to a medicinal product for topical use for the promotion of wound healing.

It is known that the healing of a wound progresses in several successive stages.

In stage I, the blood plasma protein fibrinogen is precipitated by thrombin so as to induce the formation of a fibrin clot, which solidifies in the presence of blood coagulation factor XIII. In the first stage which takes only minutes bleeding is controlled and the wound area is sealed.

In stage II, cells from the wound area migrate into the fibrin clot, i.e., inflammatory cells, connective tissue cells and endothelial cells. They form vessels and, as an extracellular matrix, connective tissue primarily comprised of collagen. This connective tissue, which is referred to as granulation tissue, serves as the substratum for the formation of epithelial tissue and is the substratum for the epidermis on the body surface. Stage II lasts for days to weeks and is complete as soon as the wound area has been closed by epithelium, and by the epidermis on the skin.

Wound healing is complete by stage III, which lasts for weeks to months. During that phase, the cellular elements are reduced and the connective tissue is growing so as to form a firm and permanent scar tissue. (Bennett N. T., Schultz G. S., Am. J. Surg. 1993, 165:728-737; Bennett N. T., Schultz G. S., Am. J. Surg. 1993, 166: 74-81).

The formation of granulation tissue in stage II of the wound healing process is effected by growth factors promoting the migration and the division of connective tissue cells as well as the regeneration of vessels and, thereby, accelerating wound healing. Of the known growth factors, platelet derived growth factor (PDGF), transforming growth factor β (TGF-β), epidermal growth factor (EGF) and insulin-like growth factor I (IGF-I) are particularly involved in those processes. (Bennett N. T., Schultz G. S., Am. J. Surg. 1993, 165: 728-737; Bennett N. T., Schultz G. S., Am. J. Surg. 1993, 166: 74-81; Bhora F. Y. et al., J. Surg. Res. 1995, 59: 236-244; Lynch S. E. et al., Proc. Natl. Acad. Sci. USA 1987, 84: 640-646; Lynch S. E. et al., J. Clin. Invest. 1989, 84: 7696-7700).

Also the regeneration of the epidermis is induced by growth factors. They activate the epidermal cells (keratinocytes) that have been detached from the cell association of the intact basal cell layer due to the lesion, so as to form specific membrane receptors enabling the adherence to the granulation tissue substratum, in particular to fibrin-fibronectin, which constitutes a provisional scaffold for keratinocyte migration (Brown G. L. et al., J. Exp. Med. 1986, 163: 1319-1324; Brown G. L. et al., N. Engl. J. Med. 1989, 321: 76-79).

Growth factors are synthesized in the human body by various tissues and cell types and secreted into the surrounding body liquid. In the context of wound healing, an important regulatory role is attributed to thrombocytes, which are able to synthesize in significant amounts and store growth factors PDGF, TGF-β, EGF and IGF-I, which are essential to wound healing in cytoplasmic granula. (Lynch S. E. et al., Proc. Natl. Acad. Sci. USA 1987; 84: 640-646; Ginsberg M. H. et al., Thromb. Haemostas. 1988, 59: 1-6; Hyner O. R., Thromb. Haemostas. 1991, 66: 40-43).

In order to release or deliver the stored growth factors from the thrombocytes, the latter must be activated by physiological stimuli such as, e.g., collagen, thrombin, trypsin, ADP, serotonin or adrenalin, which bind to specific receptors on the external surface of the thrombocyte plasma membrane. Activation results in a change of shape followed by the aggregation of thrombocytes, whereupon the latter secrete the stored growth factors into the surrounding body liquid. With most of these physiological stimuli, the aggregation of thrombocytes following activation is a prerequisite for the release of growth factors. By stimulation with thrombin, growth factors may be released also without thrombocyte aggregation. (Kaplan K. L. et al., Blood 1979, 53: 604-618; Holmsen H. et al., J. Biol. Chem. 1981, 256: 9393-9396; Philipps D. R., Baughan A. K., J. Biol. Chem. 1983, 258: 10240-10245).

The interactions between activated thrombocytes, which lead to aggregation, and their adherence to surfaces are mediated by extracellular adhesive matrix proteins such as, e.g., fibrinogen, fibronectin and von Willebrand factor, which bind to a glycoprotein receptor on the external side of the plasma membrane of the activated thrombocytes. Strong binding of these matrix proteins to the receptor is effected only where thrombocytes have been activated by an appropriate stimulus as described above. These complex procedures of thrombocyte activation and aggregation followed by the release of growth factors constitute one of the essential control elements in the wound healing process. (Ginsberg M. H. et al., Thromb. Haemostas. 1988, 59: 1-6; Hyner O. R., Thromb. Haemostas. 1991, 66: 40-43; Landolfi R. et al., Blood 1991, 78: 377-381; Perschke E. I. et al., Blood 1980, 55: 841-847; Hynes O. R., Cell 1992, 69: 11-25; Perschke E. I., J. Lab. Clin. Med. 1994, 124: 439-446; Savage B., Ruggeri Z. M., J. Biol. Chem. 1991, 266: 11227-11233; Bennett J. S. et al., J. Biol. Chem. 1982, 257: 8049-8054; Cierniewski C. S. et al., Biochim. Biophys. Acta 1982, 714: 543-548; Philipps D. R., Baughan A. K., J. Biol. Chem. 1983, 258: 10240-10245).

Disturbances in wound healing as these occur, for instance, in patients with diabetes, venous or arterial occlusions, but also wound healing disturbances of other geneses such as, for instance, irradiation with radioactive substances or after burns particularly affect stage II of the wound healing process. It has been found that in such cases growth factors are present to a reduced extent so that no or only a low quality granulation tissue is formed. (Dvonch V. M. et al., Surgery 1992, 112: 18-23; Matsuoka J., Grotendorst G. R., Proc. Natl. Acad. Sci. USA 1989, 86: 4416-4420).

In order to enhance wound healing in the case of wound healing disturbances, growth factors are known to be applied to the wound area, either individually or in combination, as a pure substance or mixed in ointment bases (Knighton D. R. et al., Surg. Gynecol. Obstet. 1990, 170: 56-60; Brown G. L. et al., J. Exp. Med. 1986, 163:1319-1324; Holmsen H. et al., J. Biol. Chem. 1981, 256: 9393-9396). The growth factors provided in this manner are, however, rapidly inactivated or degraded and develop their activities only over short periods of time (minutes) after application. Thus, these preparations offer no satisfactory enhancement of wound healing.

Other known therapeutic approaches consist in covering the wound area with collagen sponges or other preparations aimed to ensure permanent humidity of the wound area or in using preparations degrading the superficial connective tissue layer of the wound area by fermentation so as to enable new connective tissue to re-grow from the wound bed (Nielsen P.

G. et al., Acta Dermato-Venerologica 1990, Suppl. 152: 1-12; Lippert P., Wolff H., Zent.bl. Chir. 1990, 115: 1175-1180). Yet, none of those hitherto applied wound dressings and preparations or medicinal products have brought satisfactory results in improving wound healing.

The object of the present invention is to provide a medicinal product which efficaciously accelerates natural wound healing processes and is capable of substantially improving wound healing where wound healing is disturbed, in particular in severe forms of wound healing disturbances, as compared to conventional therapies.

In accordance with the invention, this object is achieved in that a medicinal product for topical use for the promotion of wound healing is provided, which comprises thrombocytes or thrombocyte fragments, wherein said thrombocytes or thrombocyte fragments contain growth factors and are capable of releasing the same, are present in the lyophilized or deep-frozen state and have been subjected to a process for virus partitioning and/or virus inactivation.

"Thrombocyte fragments" is intended to denote any insoluble thrombocyte constituents that are separable from the soluble thrombocyte constituents either by filtration including nano-filtration or by centrifugation including ultra-centrifugation.

Unless indicated otherwise, the term "thrombocytes" in the following also encompasses "thrombocyte fragments".

The invention is based on the finding that the topical use of thrombocytes containing growth factors and capable of releasing the same can efficaciously accelerate wound healing processes. The thrombocytes applied on the wound area constitute a natural reservoir for the growth factors required for the promotion of the wound healing processes. It has been found that the activation of locally applied thrombocytes by physiological stimuli present in the wound area and the subsequent aggregation and binding of the matrix proteins present in the wound area lead the growth factors stored in the thrombocytes to be released into the wound area continuously over an extended period of time (several days). Due to this fact, higher concentrations of growth factors are apparently available in the wound area over a substantially longer period of time than with the direct administration of growth factors, thereby promoting the immigration of inflammatory cells, connective tissue cells and endothelial cells and enhancing the propagation of said cells in stage II of the wound healing process. In that manner, the rapid and sufficient formation of granulation tissue is ensured, which, in turn, renders possible the formation of epithelial tissue and the final wound closure. The epithelialization process, moreover, is additionally accelerated by the released growth factors promoting the immigration and proliferation of epithelial cells.

To ensure that the medicinal product can be stored over an extended period of time, the thrombocytes in the medicinal product according to the invention preferably are present in the lyophilized or deep-frozen state. In order to minimize the risk of virus infections, the thrombocytes advantageously are subjected to a process for virus partitioning and/or virus inactivation, whereby a physical or a chemical or a combined process may be used.

In order to provide for a higher concentration of growth factors, in particular in the treatment of wound healing disturbances, it is preferred that the content of thrombocytes or thrombocyte fragments of the medicinal product according to the invention is such that it corresponds to at least $10^4$, preferably at least $10^5$, thrombocytes per µl after reconstitution of the lyophilisate or thawing.

In order to obtain a particularly pronounced initial effect of the medicinal product according to the invention immediately upon application, it may be appropriate, in particular in the case of severe disturbances of wound healing, that the medicinal product comprises additional growth factors that are not derived from the thrombocytes contained in the medicinal product. The additional growth factors may be of the same type as those stored and released by the thrombocytes of the medicinal product according to the invention or belong to a different type. The growth factors may be present in the same container with the thrombocytes or contained in a separate container in the form of a solution or lyophilisate.

It has been found that it is advantageous, in particular in severe cases of disturbed wound healing, that the medicinal product comprises biomaterials. "Biomaterials" in the sense of the invention is intended to comprise any materials which are tissue-compatible and absorbable and assist in the promotion of wound healing either in combination with the thrombocytes or growth factors contained in the medicinal product or independently thereof. Thus, substances activating thrombocytes as stimuli and/or materials mediating thrombocyte aggregation may be contained as biomaterials in the medicinal product according to the invention. In that manner, the activity of natural substances present in the wound area which activate thrombocytes and mediate their aggregation is enhanced, which increases the release of growth factors and promotes wound healing even further.

In order to minimize the risk of virus infections, the biomaterials preferably are subjected to a process for virus partitioning and/or virus inactivation, wherein a physical or chemical process or a combined process may be applied. The biomaterials may be subjected to such a process either individually or mixed with other components of the medicinal product (e.g., thrombocytes).

To ensure that the medicinal product can be stored over an extended period of time, the biomaterials in the medicinal product according to the invention advantageously are present in the lyophilized or deep-frozen state. In that case, the biomaterials may be present in the same containers with the thrombocytes and/or growth factors or contained in separate containers and deep-freezing or lyophilization of the biomaterials may be effected individually or in mixture with other components of the medicinal product.

It is known that the activation and aggregation of thrombocytes and hence the release of growth factors stored in the thrombocytes is enabled by the attachment of matrix proteins. Moreover, such proteins may form cross-linked structures to which the thrombocytes adhere and firmly bind to the wound area, such structures promoting the diffusion of growth factors to the wound area and the immigration of cells from the wound area. Accordingly, a preferred embodiment of the medicinal product according to the invention is characterized in that tissue adhesive and/or collagen are provided as biomaterials. Tissue adhesive in the sense of the invention is intended to encompass biomaterials totally or partially consisting of cross-linkable proteins suitable for tissue adhesion.

Fibrinogen is a particularly active substance for triggering the aggregation of activated thrombocytes, while thrombin represents one of the most active substances for the activation of thrombocytes. It is, therefore, advantageous for an increase in the release of growth factors and an enhancement of wound healing that the tissue adhesive is composed of fibrinogen-containing proteins and thrombin.

It has been shown that human cells such as keratinocytes, epithelial cells, embryonic and fetal cells as well as cell constituents such as liposomes are able to additionally accelerate thrombocyte-promoted wound healing and cell propagation. It is, therefore, preferred that the medicinal product additionally comprises epithelial cells and/or keratinocytes and/or embryonic and/or fetal cells and/or liposomes. The cells or the liposomes may be present as a liquid or deep-frozen suspension or as a lyophilisate in separate containers, or one or several of the mentioned cell types or liposomes either without or with any of the other components of the medicinal product in common containers.

In order to minimize the risk of virus infections, the cells or the liposomes may have been subjected to a process for virus partitioning and/or virus inactivation, whereby a physical or a chemical process or a combined process may be used. The cells or the liposomes may be subjected to such a process either individually or mixed with other components of the medicinal product.

The invention also relates to the use of thrombocytes or thrombocyte fragments containing growth factors for the production of a medicinal product for topical use for the promotion of wound healing.

Preferred embodiments of the invention will now be explained in more detail by way of examples.

EXAMPLE 1

Preparation of a Medicinal Product According to the Invention

A human thrombocyte concentrate or concentrate of thrombocyte constituents is anticoagulated by 3% sodium citrate and centrifuged (1000 g/20 min) in order to eliminate plasma and other cell constituents. The thrombocyte-rich supernatant, or supernatant of thrombocyte constituents, is suspended in RPMI medium and washed three times in RPMI medium (1000 g/20 min). The washed thrombocytes, or the washed thrombocyte constituents, are suspended in RPMI medium and adjusted to a concentration of at least $6 \times 10^5$ thrombocytes or thrombocyte constituents per µl. After this, the thrombocyte suspension is subjected to a virus inactivation process according to Example 3 and subsequently deep-frozen or lyophilized in accordance with the methods described below, thereby obtaining a medicinal product according to the invention.

Deep-freezing: 1 ml of the thrombocyte suspension is each shock deep-frozen at $-80°$ C. within 30-40 minutes and stored in a deep-frozen state. Before use, the thrombocyte concentrate is thawed at room temperature.

Lyophilization: 1 ml of the thrombocyte suspension is each shock deep-frozen at $-80°$ C. for at least 24 hours and subsequently lyophilized at $-20°$ C. to $-40°$ C. in vacuo for 20 to 24 hours. The lyophilized thrombocytes are stored at between $-20°$ C. and $-80°$ C. and rehydrated with 1 ml RPMI medium before use.

EXAMPLE 2

Preparation of a Medicinal Product According to the Invention Comprising Biomaterials The virus-inactivated thrombocyte suspension prepared according to Example 1 is supplemented with a solution of cross-linkable human protein (either fibrinogen, fibronectin, blood coagulation factor XIII or collagen) which may have been subjected to one or several processes for virus inactivation according to Example 4, each protein type separately or together in combination, wherein the concentration of the cross-linkable protein types in the supplemented solution preferably is to amount to 70-90 mg/ml. The mixing ratio of the thrombocyte suspension to the solution of cross-linkable human protein preferably is to be 1:3. The thus obtained mixture is deep-frozen or lyophilized in accordance with the processes described in Example 1 in order to obtain suitable storability.

Instead of carrying out virus inactivation on individual components (thrombocytes or biomaterials), it is also possible to effect virus inactivation on a mixture of thrombocyte suspension and protein solution according to the process of Example 3.

EXAMPLE 3

Virus Inactivation of Thrombocyte Suspension (Photodynamic Virus Inactivation)

To 50 ml of the thrombocyte suspension prepared according to Example 1 is added 8-methoxypsoralen (dissolved in dimethylsulfoxide [DMSO]) until a final concentration of 300 µl/ml (final concentration of DMSO 0.3%) and irradiated with ultraviolet light from below and above for 6 hours at 22-27° C. under an atmosphere of 5% $CO_2$ and 95% $N_2$ and at a pressure of 2 psi such that the overall light intensity is 3.5 to 4.8 $mW/cm^2$ (Lin L. et al., Blood 1989, 74: 517-525).

After photoinactivation has been completed, the thrombocyte suspensions obtained in that manner are examined for their functional capacities. The functional capacity is determined by measuring [$^3$H]-thymidine incorporation in a fibroblast cell culture.

EXAMPLE 4

Virus Inactivation of Biomaterials (Chemical Virus Inactivation)

Biomaterials which are admixed to the thrombocyte suspension prepared according to Example 1 are virus inactivated by a solvent detergent method. To this end, a biomaterial suspension is supplemented with 1% (w/w) tri(n-butyl) phosphate and 1% (w/w) Triton X-100 at 30° C. and the mixture is kept for 4 hours under shaking. After this, the solvent detergent mixture under the addition of 5% (v/v) soybean oil is removed from the biomaterial suspension by chromatography on a C18-column (Waters Millipore) (Horowitz B. et al., Blood 1992, 79: 826-831; Piet M. P. J. et al., Transfusion 1990, 30:591-598; Piquet Y. et al., Vox sang. 1992, 63: 251-256).

The biomaterials treated by the above-described chemical virus inactivation method may subsequently be subjected to photodynamic virus inactivation in addition.

EXAMPLE 5

Evaluation of the Promotion of Connective Tissue Proliferation by the Medicinal Product According to the Invention The test was carried out on a fibroblast cell culture. The medicinal product prepared according to Example 2 was applied on a cell culture plate in an amount of 200 µl per $cm^2$ and activated by 50 µl of a thrombin solution (3.2 IU thrombin per ml physiological saline). Human fibroblasts derived from the $4^{th}$ to $10^{th}$ passages of a primary culture were placed on the applied suspension at a density of $4 \times 10^4$ cells per $cm^2$ and cultivated in cell culture medium (RPMI) (culture 1). On the third, fifth and seventh days of cultivation, the cell mitotic rate was measured by measuring DNA synthesis via [$^3$H]-thymidine incorporation. The cell mitotic rate of culture 1 was compared to the cell mitotic rate of another fibroblast culture (culture 2) realized in RPMI nutrient supplemented with 10% by vol. of calf serum without addition of the medicinal product according to the invention.

Results: On day 3 of cultivation, culture 1 exhibited a [$^3$H]-thymidine incorporation (196645±56864 cpm/ml) that was seven times higher than that of culture 2. On days 5 (152749±93951 cpm/ml) and 7 (77045±27974 cpm/ml) [$^3$H]-thymidine incorporation in culture 1 still was 5 to 10 times higher than that of culture 2. These differences between culture 1 and culture 2 statistically are highly significant ($p<0.01$), demonstrating the ability of the medicinal product according to the invention to promote connective tissue proliferation and maintain that activity over an extended period of time (at least 7 days).

EXAMPLE 6

Evaluation of the Binding of Matrix Proteins to Thrombocyte Surfaces Resulting in the Thrombocyte Stored Growth Factors to be Continuously Released The test was carried out on a fibroblast culture (according to Example 5). Culture 1—as in Example 5—was supplemented with the medicinal product according to: the invention. In culture 2, the thrombocytes were treated with specific antibodies against the superficial binding sites for matrix proteins so as to prevent the matrix proteins from binding to thrombocyte surfaces. On the third day of cultivation, the cell mitotic rate was measured by measuring DNA synthesis via [$^3$H]-thymidine incorporation.

Results: While culture 1 exhibited a thymidine incorporation rate similar to that of Example 5, no thymidine incorporation could be measured in culture 2. That difference proves that the binding of matrix proteins to the thrombocyte surfaces is necessary for the thrombocyte stored growth factors to be released.

EXAMPLE 7

Evaluation of the Promotion of Wound Healing by the Medicinal Product According to the Invention The clinical efficacy of the medicinal product according to the invention was studied in six patients suffering from chronic, non-healing cutaneous ulcera of the lower extremities and already treated by surgical or conservative topical therapies for more than six months without success. The ulcera were classified using a wound score according to Knighton D. R. et al., Ann. Surg. 1986, 204:322-330. The wound score includes general parameters, anatomical conditions and measurable variables of the ulcus. The higher the scores, the poorer the preconditions for healing; the highest score to be reached is 97 (=worst starting situation).

Treatment Plan:

The ulcera were cleaned, necrotic tissue was removed and wetted with a thrombin solution (3.2 IU bovine thrombin/ml RPMI medium). After this, the defect was filled up with the thawed medicinal product according to the invention prepared according to Example 2, and the above-mentioned thrombin solution was then applied at a volume ratio of medicinal product suspension to thrombin solution of 3:1 in order to activate the thrombocytes. The ulcera treated in that manner were covered by a non-adhering wound dressing (metal foil). Until healing, the ulcera were treated twice a week in the above-identified manner. The healing progress was documented photographically and histologically (fine needle biopsies in the $2^{nd}$ and $5^{th}$ weeks of treatment).

Results:

The demographics, causative vascular and metabolic diseases of the patients and the evaluation of the wound scores at the beginning of treatment are summarized in Table 1.

TABLE 1

| Patient | Sex | Age | Vascular Disease arterial | Vascular Disease venous | Metabolic disease | Wound Score |
|---|---|---|---|---|---|---|
| 1 | male | 67 | + | + | diabetes | 51 |
| 2 | male | 72 | + | − | − | 65 |
| 3 | male | 69 | + | − | diabetes | 33 |
| 4 | male | 63 | + | − | diabetes | 49 |
| 5 | male | 78 | + | + | diabetes | 63 |
| 6 | female | 74 | − | + | − | $65^a/63^b$ |

$^{a,b})$ two ulcera on one leg:
$^a)$ proximal,
$^b)$ distal ulcus

The time course of wound healing (indicated in weeks as of the beginning of treatment) is illustrated in Table 2.

TABLE 2

| Patient | Beginning of Granulation Tissue Formation | Beginning of Epithelization | Completion of Epithelization |
|---|---|---|---|
| 1 | 1st week | 3rd week | 8th week |
| 2 | 1st week | 3rd week | 9th week |
| 3 | 3rd week | 8th week | 12th week |
| 4 | 1st week | 4th week | 10th week |
| 5 | 1st week | none | none |
| 6 | $^{a,b}$1st week | $^a$6th/$^b$3rd week | $^a$12th/$^b$9th week |

$^{a,b})$ two ulcera on one leg:
$^a)$ proximal,
$^b)$ distal ulcus

With exception of patient 3, a granulation tissue well supplied with blood formed starting from the bottom of the ulcus in all of the patients already within the first week of treatment, which granulation tissue increased upon further treatment with the medicinal product according to the invention until approximately two weeks after the beginning of the therapy and filled up the ulcus. It was striking that already after the first days of treatment the surrounding of the ulcus calmed down, the erythema and the edema of the surrounding skin disappeared and also the edge of the ulcus was no longer edematous and miscolored in all of the patients. Histologically, cell-rich granulation tissue primarily consisting of fibroblasts and fibrocytes and exhibiting intensive new vascular formation and collagenous fiber formation and only a slight infiltration of inflammatory cells and tissue necroses on the surface was to be seen in all biopsies in the second week of treatment. Epithelization of the skin defects after the third week of treatment started from the edges of the wound and could then also be detected histologically by the second biopsies in the fifth week of treatment. In the further course of treatment, the size of the ulcera declined due to epithelization, but also to cicatricial shrinkage. With the exception of patient 5, they were scarred over in the 12th week of treatment at the latest.

The results indicated above demonstrate that the topical use of the medicinal product according to the invention promotes wound healing and, thus, is able to completely cure chronically non-healing cutaneous ulcera in patients treated by conservative therapies for at least six months without success and, thus, offering extremely poor prognoses for wound healing.

The invention claimed is:

1. A medicinal product for topical use for the promotion of wound healing comprising a therapeutically effective amount of insoluble thrombocyte fragments, wherein said insoluble thrombocyte fragments (i) contain an effective amount of active growth factors and are capable of releasing the growth factors, (ii) have been prepared by a method comprising washing followed by a procedure selected from the group consisting of lyophilization and freezing, and (iii) have been subjected to a process selected from the group consisting of virus partitioning and virus inactivation, and wherein the insoluble thrombocyte fragments have not been fixed.

2. The medicinal product according to claim 1, wherein the insoluble thrombocyte fragments are present in an amount corresponding to at least $10^4$ thrombocytes fragments per ml after reconstitution of the lyophilisate or thawing.

3. The medicinal product according to claim 1, wherein the medicinal product comprises additional growth factors.

4. The medicinal product according to claim 1, wherein the medicinal product comprises a cross-linkable human protein selected from the group consisting of fibrinogen, fibronectin, blood coagulation factor XIII and collagen.

5. The medicinal product according to claim 4, wherein the cross-linkable human protein has been subjected to a process selected from the group consisting of virus partitioning and virus inactivation.

6. The medicinal product according to claim 4, wherein the cross-linkable human protein is present in the lyophilized or frozen state.

7. The medicinal product according to claim 4 wherein the cross-linkable human protein is fibrinogen.

8. The medicinal product according to claim 1, further comprising a tissue adhesive composed of fibrinogen-containing proteins.

9. The medicinal product according to claim 4, wherein the medicinal product further comprises a component selected from the group consisting of epithelial cells, keratinocytes, embryonic cells, fetal cells, liposomes and combinations thereof.

10. The medicinal product according to claim 1, further comprising a thrombocyte activating stimulus.

11. The medicinal product according to claim 5, wherein the cross-linkable human protein is present in the lyophilized or frozen state.

12. The medicinal product according to claim 5, wherein the cross-linkable human protein is fibrinogen, wherein the medicinal product further comprises a thrombocyte activating stimulus and wherein the thrombocyte activating stimulus is thrombin.

13. The medicinal product according to claim 6, wherein the cross-linkable human protein is fibrinogen, wherein the medicinal product further comprises a thrombocyte activating stimulus and wherein the thrombocyte activating stimulus is thrombin.

14. The medicinal product according to claim 10, further comprising a tissue adhesive composed of fibrinogen-containing proteins, wherein the thrombocyte activating stimulus is thrombin, and wherein the tissue adhesive and thrombin have been subjected to a process selected from the group consisting of virus partitioning and virus inactivation.

15. The medicinal product according to claim 1, further comprising a tissue adhesive composed of fibrinogen-containing proteins and wherein the tissue adhesive is present in the lyophilized or frozen state.

16. The medicinal product according to claim 5, wherein the medicinal product additionally comprises a component selected from the group consisting of epithelial cells, keratinocytes, embryonic cells, fetal cells, liposomes and combinations thereof.

17. The medicinal product according to claim 6, wherein the medicinal product additionally comprises a component selected from the group consisting of epithelial cells, keratinocytes, embryonic cells, fetal cells, liposomes and combinations thereof.

18. The medicinal product according to claim 7, wherein the medicinal product additionally comprises a component selected from the group consisting of epithelial cells, keratinocytes, embryonic cells, fetal cells, liposomes and combinations thereof.

19. The medicinal product according to claim 8, wherein the medicinal product additionally comprises a component selected from the group consisting of epithelial cells, keratinocytes, embryonic cells, fetal cells, liposomes and combinations thereof.

* * * * *